United States Patent
Rehwald

(10) Patent No.: US 11,547,317 B2
(45) Date of Patent: Jan. 10, 2023

(54) TI SCOUT FOR INVERSION RECOVERY SEQUENCE

(71) Applicant: Siemens Healthcare GmbH, Erlangen (DE)

(72) Inventor: Wolfgang G. Rehwald, Chapel Hill, NC (US)

(73) Assignee: Siemens Healthcare GmbH, Erlangen (DE)

( * ) Notice: Subject to any disclaimer, the term of this patent is extended or adjusted under 35 U.S.C. 154(b) by 713 days.

(21) Appl. No.: 16/385,026

(22) Filed: Apr. 16, 2019

(65) Prior Publication Data

US 2020/0237253 A1 Jul. 30, 2020

Related U.S. Application Data

(60) Provisional application No. 62/796,286, filed on Jan. 24, 2019.

(51) Int. Cl.
*A61B 5/055* (2006.01)
*G01R 33/54* (2006.01)
(Continued)

(52) U.S. Cl.
CPC ............ *A61B 5/055* (2013.01); *A61B 5/0033* (2013.01); *G01R 33/543* (2013.01); *G01R 33/56* (2013.01)

(58) Field of Classification Search
CPC ...... A61B 5/055; G01R 33/543; G01R 33/56; G01R 33/5601; G01R 33/5602; G01R 33/5607; G01R 33/5673
See application file for complete search history.

(56) References Cited

U.S. PATENT DOCUMENTS

2005/0165295 A1* 7/2005 Li ................ G01R 33/56
600/410
2006/0161060 A1* 7/2006 Pai ............. G01R 33/563
600/431

(Continued)

OTHER PUBLICATIONS

H.W. Kim et al. "Dark-Blood Delayed Enhancement Cardiac Magnetic Resonance of Myocardial Infarction." J Am Coll Cardiol Img. Dec. 2018, 11 (12) 1758-1769; Published online Dec. 13, 2017 at JACC Journals (Year: 2017).*

(Continued)

*Primary Examiner* — Keith M Raymond
*Assistant Examiner* — Milton Truong

(57) ABSTRACT

A system comprises determination of an inversion-recovery or saturation-recovery imaging pulse sequence associated with first values of echo spacing, flip angle, effective TR, trigger pulses, artifact post-suppression, and number of image data lines per acquisition, execution of a scout pulse sequence comprising a plurality of single-shot image data acquisitions to acquire respective sets of image data lines, where each of the plurality of single-shot image data acquisitions is executed using a different respective inversion time and where each of the plurality of single-shot image data acquisitions is associated with second values of echo spacing, flip angle, and number of image data lines per acquisition which are substantially similar to corresponding ones of the first values, generation of a plurality of images based on the respective sets of image data lines, determination of one of the plurality of images, the determined one of the plurality of images generated based on a set of image data lines acquired using a first inversion time, and execution of the inversion-recovery or saturation-recovery imaging pulse sequence using the first inversion time.

20 Claims, 6 Drawing Sheets

(51) Int. Cl.
  *G01R 33/56* (2006.01)
  *A61B 5/00* (2006.01)

(56) References Cited

U.S. PATENT DOCUMENTS

| | | | |
|---|---|---|---|
| 2014/0314289 A1* | 10/2014 | Spottiswoode | G06T 7/0012 |
| | | | 382/128 |
| 2015/0123659 A1* | 5/2015 | Weingartner | G01R 33/50 |
| | | | 324/309 |
| 2017/0212195 A1* | 7/2017 | Rehwald | G01R 33/5602 |
| 2018/0217217 A1* | 8/2018 | Weingartner | G01R 33/50 |
| 2018/0303374 A1* | 10/2018 | Marrouche | G01R 33/5673 |
| 2020/0256939 A1* | 8/2020 | Wang | G01R 33/4822 |

OTHER PUBLICATIONS

W. Rehwald et al. "A Novel Single-Cardiac-Cycle Phase Sensitive Inversion Recovery (PSIR) Method Improves Free Breathing Single Shot Flow Independent Dark Blood Delayed Enhancement (FIDDLE)". 20th Annual SCMR Scientific Sessions Abstract Supplement, 2017: p. 386 (Year: 2017).*

C. Farrelly et al. "Improved Detection of Subendocardial Hyperenhancement in Myocardial Infarction Using Dark Blood-Pool Delayed Enhancement MRI". AJR 2011; 196:339-348 (Year: 2011).*

Messroghli, Daniel R. et al. Modified Look-Locker Inversion Recovery (MOLLI) for High-Resolution T1, Mapping of the Heart, Magnetic Resonance in Medicine, 52:141-146 (2004), 6 pages.

Amano, Yasuo, "Contrast-Enhanced Myocardial T-1-Weighted Scout (Look-Locker) Imaging for the Detection of Myocardial Damages in Hypertrophic Cardiomyopathy", Journal of Magnetic Resonance Imaging 30, pp. 778-784, 2009, 7 pages.

Pandey, Tarun et al., "Utility of the inversion scout sequence (TI scout) in diagnosing myocardial amyloid infiltration", International Journal Cardiovascular Imaging, NIH Public Access, Author Manuscript, Jan. 29, 2013, 16 pages.

* cited by examiner

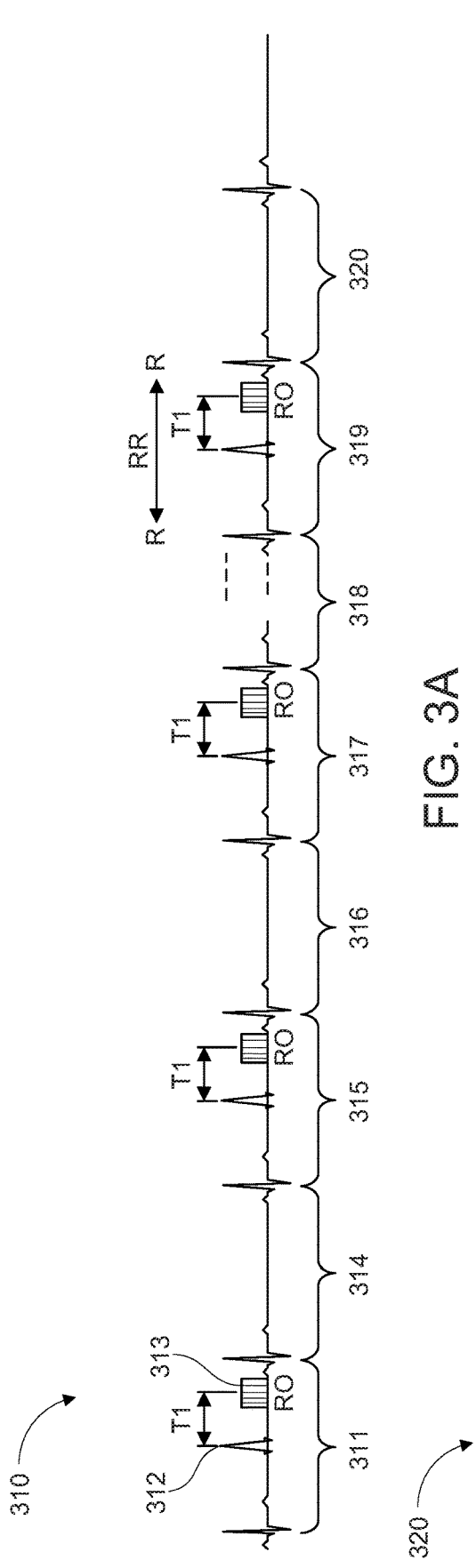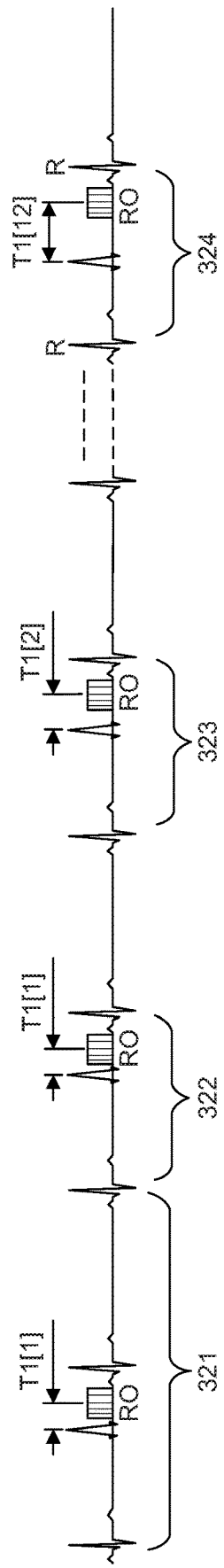
FIG. 3A
FIG. 3B

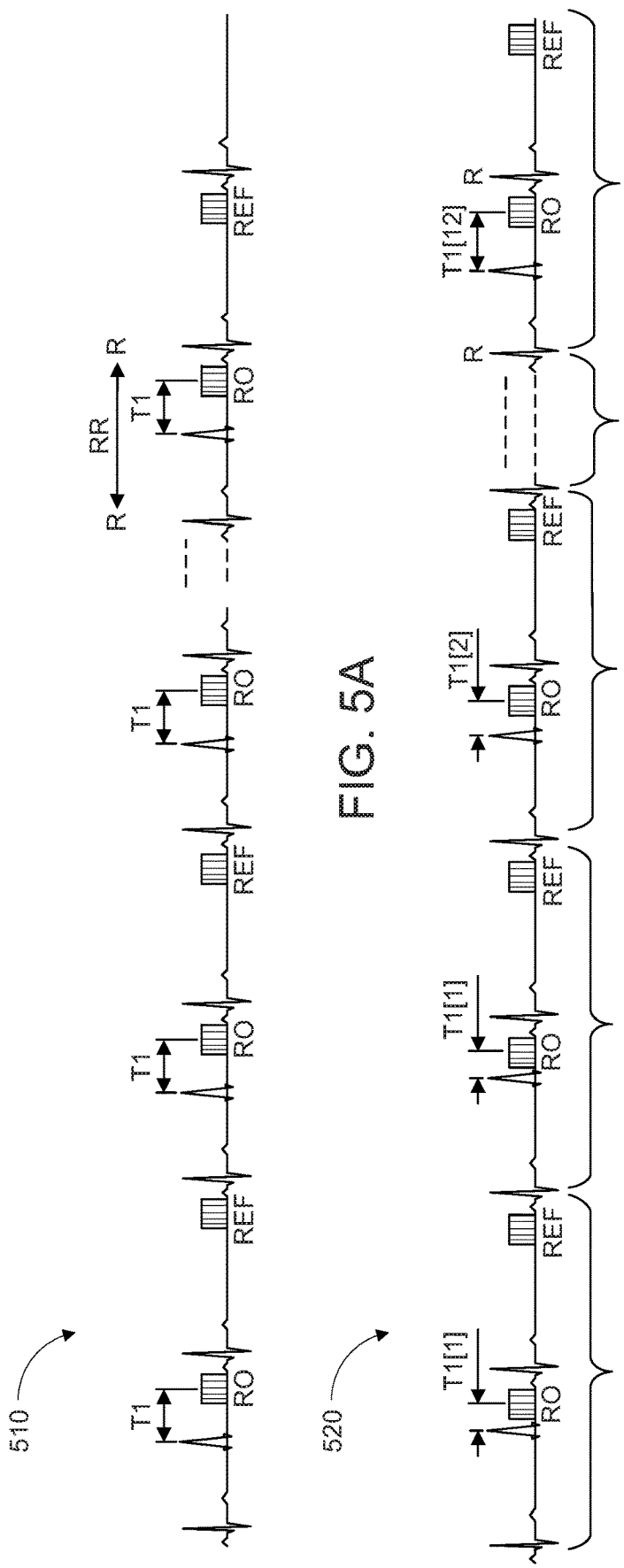

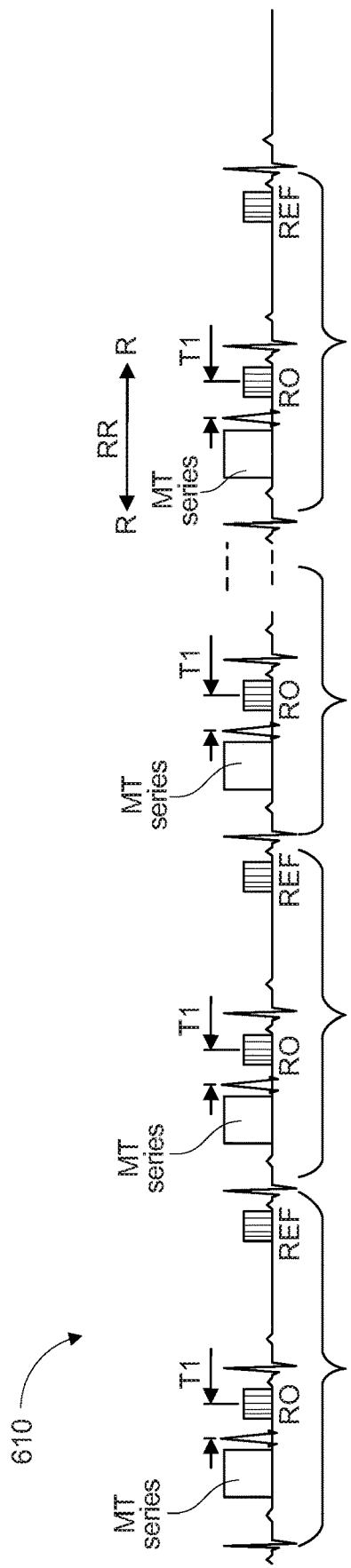
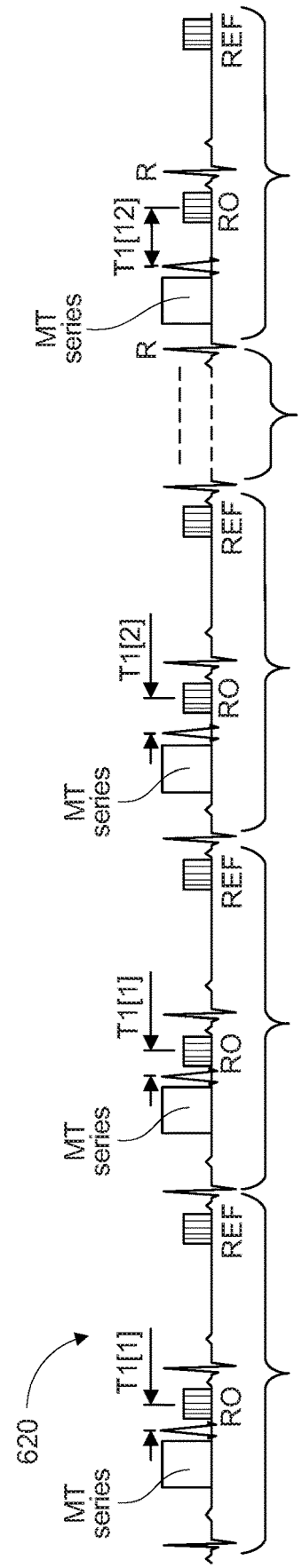
FIG. 6A
FIG. 6B

TI SCOUT FOR INVERSION RECOVERY SEQUENCE

CROSS-REFERENCE TO RELATED APPLICATIONS

The present application claims priority to U.S. Provisional Patent Application No. 62/796,286, filed Jan. 24, 2019, the contents of which are incorporated by reference herein for all purposes.

BACKGROUND

A Magnetic Resonance (MR) scanner generates images of patient anatomy based on sequences of RF pulses. According to a typical inversion recovery (IR) sequence, an R-wave of the cardiac cycle is detected, an inversion pulse is delivered after a first waiting period, and raw image data is read after a second waiting period. The second waiting period between the inversion pulse and the contrast-relevant readout line is known as the "inversion time" (TI).

Different values of TI result in different T1 weighting of the image data, which results in different contrast levels between tissue types. In the case of a short TI, magnetization of all tissues will be similarly inverted at readout regardless of differences in the tissues, and the tissues will appear similar in the resulting image. For longer TIs, tissues with shorter T1 properties will recover faster and generate a greater positive signal than other tissues with longer T1 properties, which will appear darker. It is therefore desirable to set the TI to achieve suitable T1-contrast between tissue types of interest.

In cardiac MR, a delayed enhancement (DE) or late Gadolinium Enhancement (LGE) sequence requires injection of a T1-shortening contrast agent into the patient. Ideally, a normal (healthy, viable) myocardium appears dark grey and infarcted myocardium ("infarct") bright in a resulting image, resulting in maximum separation of normal and infarcted tissue while still visualizing the morphology of normal myocardium. Since the contrast agent continuously washes out of tissue and blood due to the clearance by the kidneys, maintaining the above-described image contrast requires continuous adjustment of the TI as a function of the continuously-changing T1 values of the imaged tissues.

This adjustment is difficult and time-consuming. Therefore, even experienced scanner operators often adjust the TI too coarsely, resulting in suboptimal contrast, which can lead to missed pathology and wrong clinical diagnosis. This problem is exacerbated in certain types of DE imaging, such as flow-independent dark blood delayed enhancement (FIDDLE) imaging, due to a small ranger of TI values which provide optimal image contrast.

Improved systems to determine appropriate TI values for IR sequences are therefore desired.

BRIEF DESCRIPTION OF THE DRAWINGS

FIG. 3a illustrates a segmented inversion recovery sequence according to some embodiments.

FIG. 3b illustrates a TI-scout pulse sequence corresponding to a segmented inversion recovery sequence according to some embodiments.

FIG. 5a illustrates a segmented phase-sensitive inversion recovery sequence according to some embodiments.

FIG. 5b illustrates a TI-scout pulse sequence corresponding to a segmented phase-sensitive inversion recovery sequence according to some embodiments.

FIG. 6a illustrates a flow-independent dark blood delayed enhancement sequence according to some embodiments.

FIG. 6b illustrates a TI-scout pulse sequence corresponding to a flow-independent dark blood delayed enhancement sequence according to some embodiments.

DETAILED DESCRIPTION

The following description is provided to enable any person in the art to make and use the described embodiments. Various modifications, however, will remain readily apparent to those in the art.

Generally, some embodiments determine a TI for a segmented DE sequence using a TI scout sequence. The TI scout sequence includes a series of single-shot acquisitions which substantially reproduce the magnetic saturation and recovery of tissue caused by the segmented DE sequence. Each single shot uses a different TI and acquires the same set of lines of raw image data. Each single-shot acquisition utilizes substantially identical parameters (e.g., readout type, flip angle, number of lines per segment readout, echo spacing, type of inversion pulse or combined IR preparation, trigger pulse, artifact post-suppression, and reference scan on/off) as the segmented DE sequence for which the TI is to be determined.

An image is generated based on each set of lines acquired by each single shot of the TI scout. The image providing the most suitable contrast between relevant tissues is selected, and the segmented DE sequence is executed using the TI associated with the selected image (i.e., the TI used to acquire the set of image data lines from which the selected image was generated). A TI scout sequence according to some embodiments may be executed once and may replace the conventional iterative and time-consuming search for a suitable segmented IR sequence TI.

By configuring the timing and magnetization-relevant parameters of the TI scout sequence to match the magnetic relaxation behavior of the segmented DE sequence, embodiments may efficiently determine a most-suitable TI for a given segmented DE sequence. This lies in contrast to prior-art sequences exist which create magnetization curves that significantly deviate from those of the intended segmented DE sequence, rendering an accurate determination of TI is impossible. Embodiments are also capable of acquiring scout images at any desired TI range and increment, because these scout images can be acquired during free breathing so that scan time is not limited by breath holding, unlike other systems which require breath holding.

The definition of "best", "most-suitable" or "optimal" TI for a given IR-based pulse sequence depends on the specific application. One example concerns the level of contrast between normal myocardium and infarcted myocardium in delayed enhancement (DE) imaging performed in the presence of a T1-shortening contrast agent. In this case an "optimal" TI provides maximal separation of infarct and normal myocardium in the resulting image while simultaneously rendering the latter dark grey or black (i.e., nulled), depending on the physician's preference.

While the examples herein are described with respect to inversion-recovery imaging pulse sequences, embodiments may also be implemented in conjunction with saturation-recovery imaging pulse sequences.

Figure 1:
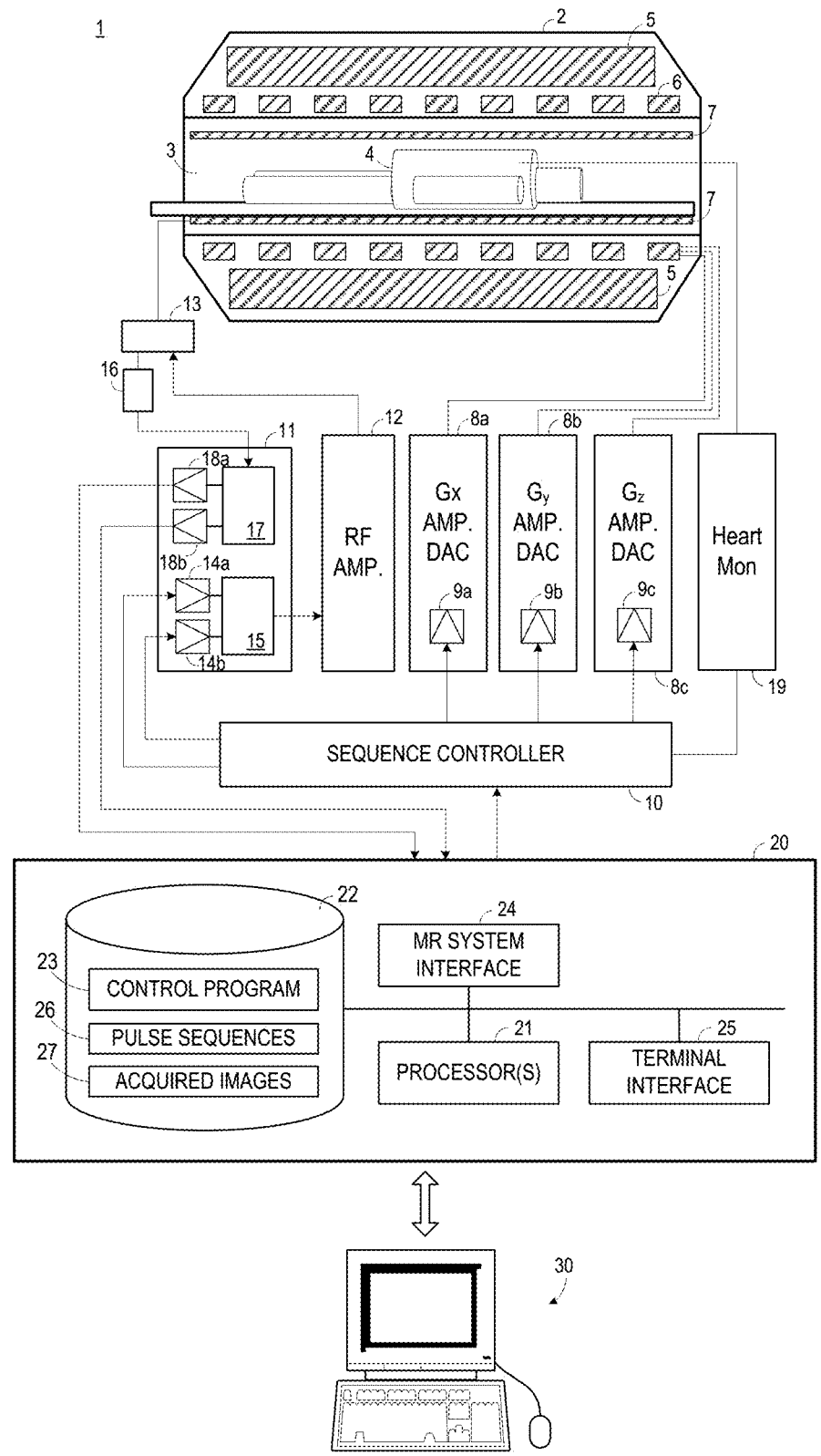
FIG. 1 is a block diagram of an MR system according to some embodiments.

FIG. 1 illustrates MR system 1 according to some embodiments. MR system 1 includes MR chassis 2, which defines bore 3 in which patient 4 is disposed. MR chassis 2 includes polarizing main magnet 5, gradient coils 6 and RF coil 7 arranged about bore 3. According to some embodiments, polarizing main magnet 5 generates a uniform main magnetic field ($B_0$) and RF coil 7 emits an excitation field ($B_1$).

According to MR techniques, a substance (e.g., human tissue) is subjected to a main polarizing magnetic field (i.e., $B_0$), causing the individual magnetic moments of the nuclear spins in the substance to process about the polarizing field in random order at their characteristic Larmor frequency, in an attempt to align with the field. A net magnetic moment $M_z$ is produced in the direction of the polarizing field, and the randomly-oriented magnetic components in the perpendicular plane (the x-y plane) cancel out one another.

The substance is then subjected to an excitation field (i.e., $B_1$) created by emission of a radiofrequency (RF) pulse, which is in the x-y plane and near the Larmor frequency, causing the net aligned magnetic moment $M_z$ to rotate into the x-y plane so as to produce a net transverse magnetic moment $M_t$, which is rotating, or spinning, in the x-y plane at the Larmor frequency. The excitation field is terminated and signals are emitted by the excited spins as they return to their pre-excitation field state. The emitted signals are detected, digitized and processed to reconstruct an image using one of many well-known MR reconstruction techniques.

An RF inversion, or saturation, pulse may be emitted as a magnetization preparation step in order to enhance or suppress signals from certain tissue so as to generate desired levels of contrast in the resulting image.

Gradient coils 6 produce magnetic field gradients $G_x$, $G_y$, and $G_z$ which are used for position-encoding NMR signals. The magnetic field gradients $G_x$, $G_y$, and $G_z$ distort the main magnetic field in a predictable way so that the Larmor frequency of nuclei within the main magnetic field varies as a function of position. Accordingly, an excitation field $B_1$ which is near a particular Larmor frequency will tip the net aligned moment $M_z$ of those nuclei located at field positions which correspond to the particular Larmor frequency, and signals will be emitted only by those nuclei after the excitation field $B_1$ is terminated.

Gradient coils 6 may consist of three windings, for example, each of which is supplied with current by an amplifier 8a-8c in order to generate a linear gradient field in its respective Cartesian direction (i.e., x, y, or z). Each amplifier 8a-8c includes a digital-analog converter 9a-9c which is controlled by a sequence controller 10 to generate desired gradient pulses at proper times.

Sequence controller 10 also controls the generation of RF pulses by RF system 11 and RF power amplifier 12. RF system 11 and RF power amplifier 12 are responsive to a scan prescription and direction from sequence controller 10 to produce RF pulses of the desired frequency, phase, and pulse amplitude waveform. The generated RF pulses may be applied to the whole of RF coil 7 or to one or more local coils or coil arrays. RF coil 7 converts the RF pulses emitted by RF power amplifier 12, via multiplexer 13, into a magnetic alternating field in order to excite the nuclei and align the nuclear spins of the object to be examined or the region of the object to be examined. As mentioned above, RF pulses may be emitted in a magnetization preparation step in order to enhance or suppress certain signals.

The RF pulses are represented digitally as complex numbers. Sequence controller 10 supplies these numbers in real and imaginary parts to digital-analog converters 14a-14b in RF system 11 to create corresponding analog pulse sequences. Transmission channel 15 modulates the pulse sequences with a radio-frequency carrier signal having a base frequency corresponding to the resonance frequency of the nuclear spins in the volume to be imaged.

RF coil 7 both emits radio-frequency pulses as described above and scans the alternating field which is produced as a result of processing nuclear spins, i.e. the nuclear spin echo signals. The received signals are received by multiplexer 13, amplified by RF amplifier 16 and demodulated in receiving channel 17 of RF system 11 in a phase-sensitive manner. Analog-digital converters 18a and 18b convert the demodulated signals into a real part and an imaginary part.

Heart monitor 19 receives signals representing the cardiac cycle of patient 4. Sequence controller 10 may detect features (e.g., an R wave) within a cardiac cycle and trigger pulses of an imaging sequence based on the detection. For cardiac imaging, such an approach may ensure that the heart is at a same point of the cardiac cycle (and in substantially the same physical position) during consecutive segment acquisitions.

Computing system 20 receives the real and imaginary parts from analog-digital converters 18a and 18b and reconstructs an image therefrom according to known techniques. System 20 may comprise any general-purpose or dedicated computing system. Accordingly, system 20 includes one or more processing units 21 (e.g., processors, processor cores, execution threads, etc.) configured to execute processor-executable program code to cause system 20 to operate as described herein, and storage device 22 for storing the program code. Storage device 22 may comprise one or more fixed disks, solid-state random access memory, and/or removable media (e.g., a thumb drive) mounted in a corresponding interface (e.g., a USB port).

Storage device 22 stores program code of control program 23. One or more processing units 21 may execute control program 23 to cause system 20 to perform any one or more of the processes described herein. For example, one or more processing units 21 may execute control program 23 to cause system 20 to execute a TI scout sequence, determine a TI, and execute an IR-based imaging sequence using the determined TI as described herein. Pulse sequences 26 include data specifying the parameters of pulse sequences and their constituent building blocks and readout events.

One or more processing units 21 may execute control program 23 to cause system 20 to receive the real and imaginary parts of a received RF signal via MR system interface 24 and reconstruct an image therefrom according to known techniques. Such an image may be stored among acquired images 28 of storage device 22.

One or more processing units 21 may also execute control program 23 to provide instructions to sequence controller 10 via MR system interface 24. For example, sequence controller 10 may be instructed to initiate a desired pulse sequence of pulse sequences 26. In particular, sequence controller 10 may be instructed to control the switching of magnetic field gradients via amplifiers 8a-8c at appropriate times, the transmission of radio-frequency pulses having a specified phase and amplitude at specified times via RF system 11 and RF amplifier 12, and the readout of the resulting magnetic resonance signals.

Acquired images 27 may be provided to terminal 30 via terminal interface 25 of system 20. Terminal interface 25 may also receive input from terminal 30, which may be used to provide commands to control program 23 in order to control sequence controller 10 and/or other elements of system 1. The commands may include commands to initiate a TI scout sequence, to select an image from among a plurality of images acquired by the TI scout sequence, and to initiate an IR-based imaging sequence using the TI associated with the identified image. Terminal 30 may simply comprise a display device and an input device coupled to system 20. In some embodiments, terminal 30 is a separate computing device such as, but not limited to, a desktop computer, a laptop computer, a tablet computer, and a smartphone.

Each element of system 1 may include other elements which are necessary for the operation thereof, as well as additional elements for providing functions other than those described herein. Storage device 22 may also store data and other program code for providing additional functionality and/or which are necessary for operation of system 20, such as device drivers, operating system files, etc.

Figure 2:
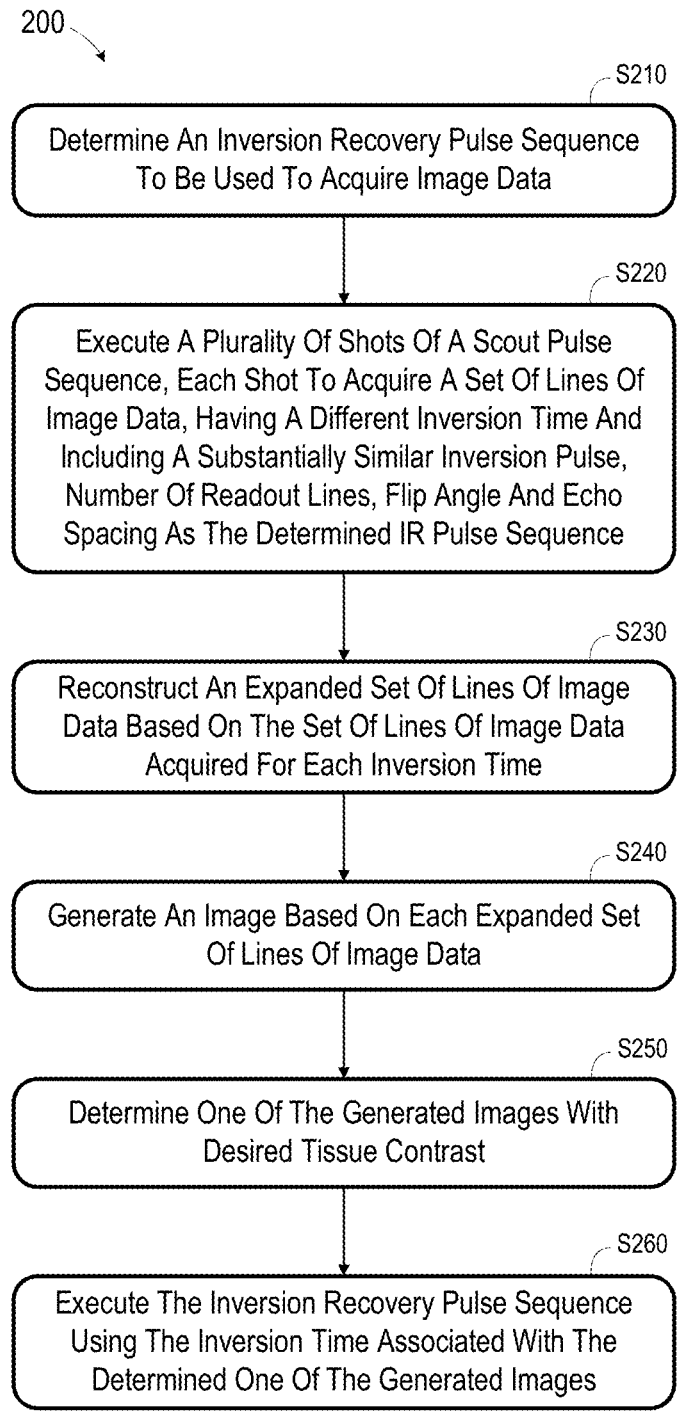
FIG. 2 comprises a flow diagram of a process according to some embodiments.

FIG. 2 is a flowchart of process 200 according to some embodiments. In some embodiments, various hardware elements of system 1 (e.g., one or more processors) execute program code to perform process 200. Process 200 and all other processes mentioned herein may be embodied in processor-executable program code read from one or more of non-transitory computer-readable media, such as a disk-based or solid-state hard drive, CD-ROM, a DVD-ROM, a Flash drive, and a magnetic tape, and then stored in a compressed, uncompiled and/or encrypted format. In some embodiments, hard-wired circuitry may be used in place of, or in combination with, program code for implementation of processes according to some embodiments. Embodiments are therefore not limited to any specific combination of hardware and software.

Initially, at S210, an inversion recovery (IR) pulse sequence is determined. The determined IR pulse sequence is intended to be used to acquire image data suitable for its intended use. For example, the determined IR pulse sequence may comprise a standard segmented IR sequence, a segmented phase-sensitive IR sequence, a flow-independent dark blood delayed enhancement sequence, or any other IR sequence that is or becomes known.

FIG. 3a illustrates conceptual pulse sequence diagram of a standard segmented IR sequence 310 that may be determined at S210 according to some embodiments. Sequence 310 acquires segmented data during a series of R-R intervals. As shown, during first R-R interval 311, inversion pulse 312 is fired to separate magnetization of normal myocardium and infarct. The tissues undergo recovery curves according to their T1 characteristics (i.e., a shorter T1 results in faster recovery) and raw image data is acquired by readout pulses 313 in accordance with inversion time TI.

R-R interval 314 is a recovery interval to allow for partial magnetization recovery. The degree of recovery depends on the duration of the R-R interval (i.e., the inverse of the heartrate). After an initial phase typically lasting two heartbeats, the magnetization curves undergo a same recovery after each inversion pulse. Undergoing the same magnetic saturation and recovery curve in a periodic manner may be considered "steady state" behavior.

Accordingly, intervals 311 and 314 may consist of dummy beats, during which the pulse sequence events are played as during the remaining run of the sequence but any acquired data is discarded. Image data acquisition therefore occurs during intervals 315-320, at which time the tissues are exhibiting steady state behavior. Sequence 310 is considered segmented because each readout of intervals 315, 317, and 319 acquires a different segment of k-space. For example, if the image is to consist of 200 lines in k-space, sequence 310 may be configured to acquire a different 20 lines (i.e., one segment) per interval over ten different intervals, each using the same TI.

Once the IR pulse sequence has been determined at S210, a scout pulse sequence is executed at S220. The scout pulse sequence includes a plurality of single-shot acquisitions, where each shot acquires a same set of lines of image data using a different inversion time (TI). Moreover, each shot uses a substantially similar inversion pulse, number of readout lines, flip angle and echo spacing as the IR pulse sequence determined at S220. Accordingly, the set of lines acquired by each shot is acquired while the tissues are behaving according to substantially the same magnetization and recovery curves as present during image acquisition using the determined IR pulse sequence.

FIG. 3b illustrates scout pulse sequence 320 reflecting the timing and magnetization properties of segmented IR sequence 310 for which it will be used to determine an optimal TI. In one example, segmented IR sequence 310 uses specific values for lines per segment (e.g., 31), flip angle (e.g., 12 degrees), echo spacing (e.g., 3.95 ms), RF spoiling (e.g., spoiling ON), and trigger pulse (e.g., 2). Accordingly, each single shot acquisition interval 322 to 324 (ignoring dummy beat intervals 321) uses substantially the same parameter values to create substantially the same magnetization as each segment-acquisition interval 315, 317, 319 of segmented IR sequence 310.

Unlike sequence 310, scout sequence 320 uses a different TI for each of its acquisitions in order to capture images having different T1-contrast. In some embodiments, the TI is modified in small increasing increments (e.g., ~20 ms) in order to create the intended contrast in a next readout, without significantly affecting the overall magnetization steady state from one acquisition to the next.

As mentioned, each acquisition interval of sequence 320 acquires a same number of image data lines (e.g., 20) as acquired in each acquisition interval of sequence 310 in order to match the magnetic evolution caused by sequence 310. Each shot of sequence 320 acquires a same set of lines of image data, albeit using a different TI. Accordingly, after executing sequence 320, multiple sets of the same image data lines have been acquired, with each set associated with a different TI.

With respect to the above-mentioned example, each successive acquisition of sequence 310 may acquire a different set of k-space image data lines (e.g., 1-20, 21-40, 41-60, . . . , 181-200). An image may be generated based on the acquired (200, for example) lines.

In contrast, because the number of lines per each set acquired by sequence 320 is significantly smaller than the number of lines used to generate an image corresponding to sequence 310, an expanded set of image data lines is reconstructed at S230 based on each set of image data lines acquired at S220. An image is then generated based on each expanded set of lines at S240.

Parallel image acquisition such as GeneRalized Autocalibrating Partial Parallel Acquisition (GRAPPA), for example, may be used to reconstruct a small number of acquired raw data lines into an image at S230 and S240. Compressed sensing could also be used to reconstruct images from the small number of acquired raw data lines. Simple interpolation of image pixels could also be used. The number of expanded image lines may be fewer than that obtained by the corresponding IR sequence (e.g., sequence 310), but the resulting images need not be of high spatial resolution since, as will be described below, the images are used at S250 only for their depiction of grey-levels of different tissue types.

Specifically, one of the generated images is determined at S250 in which the imaged tissues exhibit the desired contrast. According to some embodiments, the image determined at S250 is the one of the generated images which exhibits maximal separation of infarct myocardium and normal myocardium and in which the normal myocardium is dark grey. S250 may be performed manually, by a computing device executing a suitable detection algorithm, or by a combination of both.

Figure 4:
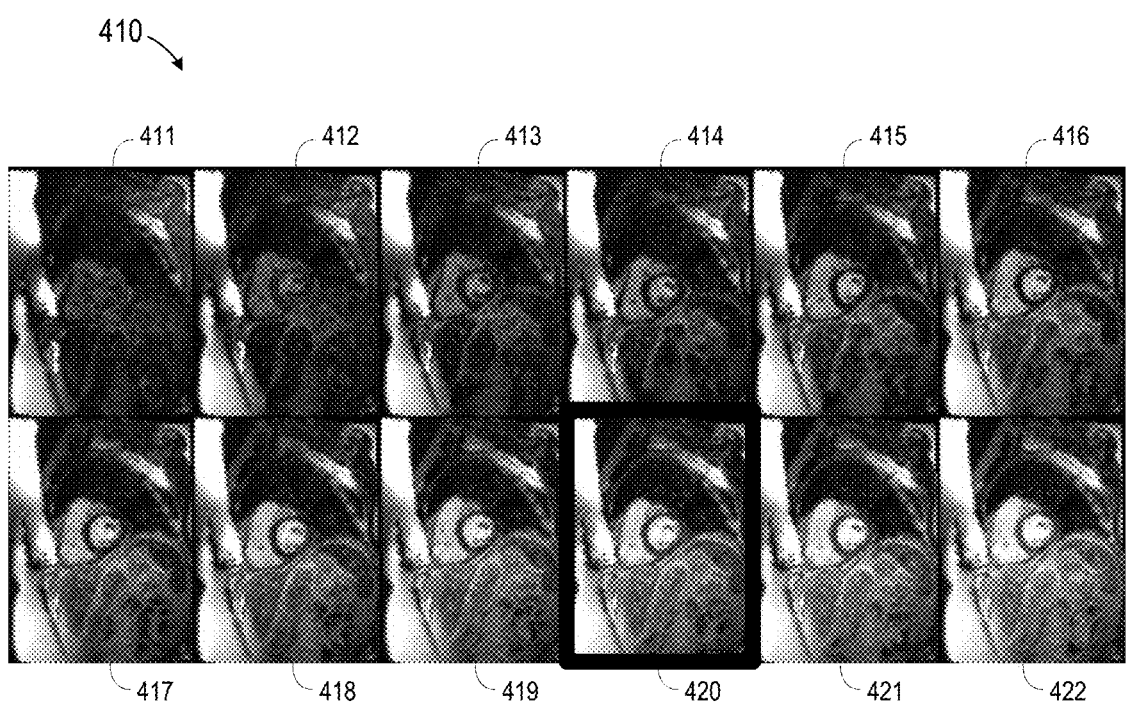
FIG. 4 illustrates images acquired using different TI values according to some embodiments.

FIG. 4 shows single-shot TI scout images 411 to 422 acquired as described above. The TI associated with each image (i.e., the TI used to acquire the raw image data used to generate the image) increases with increasing reference numeral. It will be assumed that image 420 is determined to exhibit the optimal myocardial image contrast. Accordingly, the IR pulse sequence determined at S210 is then executed using the TI associated with image 420 at S250. The resulting image should therefore also exhibit the optimal contrast of the image determined at S250.

FIG. 5a illustrates segmented phase-sensitive inversion recovery (P SIR) sequence 510 which may be determined at S210 according to some embodiments. Sequence 510 is similar to sequence 310 except that reference data (REF) is acquired during the recovery intervals. The reference data is used to reconstruct sign-true images (known as PSIR images) as opposed to the magnitude images of the standard segmented IR sequence. The reference data readout causes small but not negligible magnetic saturation which can affect the optimal TI for sequence 510. Therefore, corresponding scout sequence 520 executed at S220 also includes these REF acquisitions. Otherwise, the characteristics of scout sequence 520 are similar to those described above to sequence 320 and process 200 may be similarly performed with respect thereto.

FIG. 6a illustrates flow-independent dark blood delayed enhancement (FIDDLE) sequence 610 which may be determined at S210 according to some embodiments. Sequence 610 is similar to sequence 510 except that a combined magnetization transfer (MT) and IR pulse tissue preparation is performed instead of an IR pulse-only tissue preparation. Corresponding scout sequence 620 executed at S220 includes the combined magnetization transfer (MT) and IR pulse tissue preparation as well as the depicted REF acquisitions. The magnetization-relevant parameter values of scout sequence 620 match those of sequence 610 as described above, with each single-shot acquisition being associated with a different TI.

The foregoing diagrams represent logical architectures for describing processes according to some embodiments, and actual implementations may include more or different components arranged in other manners. Other topologies may be used in conjunction with other embodiments. Moreover, each component or device described herein may be implemented by any number of devices in communication via any number of other public and/or private networks. Two or more of such computing devices may be located remote from one another and may communicate with one another via any known manner of network(s) and/or a dedicated connection. Each component or device may comprise any number of hardware and/or software elements suitable to provide the functions described herein as well as any other functions. For example, any computing device used in an implementation of a system according to some embodiments may include a processor to execute program code such that the computing device operates as described herein.

All systems and processes discussed herein may be embodied in program code stored on one or more non-transitory computer-readable media. Such media may include, for example, a floppy disk, a CD-ROM, a DVD-ROM, a Flash drive, magnetic tape, and solid state Random Access Memory (RAM) or Read Only Memory (ROM) storage units. Embodiments are therefore not limited to any specific combination of hardware and software.

Embodiments described herein are solely for the purpose of illustration. Those in the art will recognize other embodiments may be practiced with modifications and alterations to that described above.

What is claimed is:

1. A system comprising:
a chassis defining a bore;
a main magnet to generate a polarizing magnetic field within the bore;
one or more gradient coils to apply a gradient magnetic field to the polarizing magnetic field;
a radio frequency (RF) coil to transmit RF pulses to patient tissue disposed within the bore and to receive signals from the patient tissue; and
a computing system to execute program code, configured to:
determine an inversion-recovery or saturation-recovery imaging pulse sequence associated with first tissue magnetization-relevant parameter values, each data acquisition of the inversion-recovery or saturation-recovery imaging pulse sequence to acquire a different set of a first number of image data lines of an image;
control the RF coil and one or more gradient coils to execute a scout pulse sequence comprising a plurality of single-shot image data acquisitions, where each of the plurality of single-shot image data acquisitions is executed using a different respective inversion time and acquires a same set of the first number of image data lines, and where each of the plurality of single-shot image data acquisitions is associated with second tissue magnetization-relevant parameter values which are substantially the same as corresponding ones of the first tissue magnetization-relevant parameter values;
generate a plurality of images, wherein each of the plurality of images is generated based on a respective set of the first number of image data lines and on no other sets of the first number of image data lines;
determine one of the plurality of images, the determined one of the plurality of images generated based on a first set of image data lines acquired using a first inversion time; and
control the RF coil to execute the inversion-recovery or saturation-recovery imaging pulse sequence using the first inversion time.

2. A system according to claim 1, wherein the first tissue magnetization-relevant parameter values comprise values for echo spacing, flip angle, effective TR, trigger pulses, and artifact post-suppression.

3. A system according to claim 2, where each of the plurality of single-shot image data acquisitions acquires a same set of the first number of k-space image data lines.

4. A system according to claim 1, where each of the plurality of single-shot image data acquisitions acquires a same set of the first number of k-space image data lines.

5. A system according to claim 1, where the inversion-recovery or saturation-recovery imaging pulse sequence is a phase-sensitive inversion-recovery imaging pulse sequence.

6. A system according to claim 5, where the inversion-recovery or saturation-recovery imaging pulse sequence is a flow-independent dark-blood delayed enhancement sequence.

7. A system according to claim 1, where the scout pulse sequence is executed during free breathing of a patient being imaged.

8. A system according to claim 1, wherein determination of one of the plurality of images comprises determination of the one of the plurality of images which exhibits maximal separation of infarct myocardium and normal myocardium.

9. A system according to claim 8, wherein determination of one of the plurality of images comprises determination of the one of the plurality of images in which the normal myocardium is dark grey.

10. A system according to claim 1, further comprising: a display to present the plurality of images.

11. A computer-implemented method comprising:
determining an inversion-recovery or saturation-recovery imaging pulse sequence associated with first values of echo spacing, flip angle, effective TR, trigger pulses, and artifact post-suppression, where each data acquisition of the inversion-recovery or saturation-recovery imaging pulse sequence is to acquire a different set of a first number of image data lines of an image;
executing a scout pulse sequence comprising a plurality of single-shot image data acquisitions to acquire respective sets of image data lines, where each of the plurality of single-shot image data acquisitions is executed using a different respective inversion time and acquires a same set of the first number of image data lines, and where each of the plurality of single-shot image data acquisitions is associated with second values of echo spacing, flip angle, effective TR, trigger pulses, and artifact post-suppression which are substantially the same as corresponding ones of the first values;
generating a plurality of images, wherein each of the plurality of images is generated based on a respective one of the sets of image data lines and on no other set of image data lines;
determining one of the plurality of images, the determined one of the plurality of images generated based on a first set of image data lines acquired using a first inversion time; and
executing the inversion-recovery or saturation-recovery imaging pulse sequence using the first inversion time.

12. A method according to claim 11, wherein each of the plurality of single-shot image data acquisitions acquires a same set of the first number of k-space image data lines.

13. A method according to claim 11, where the inversion-recovery or saturation-recovery imaging pulse sequence is a phase-sensitive inversion-recovery imaging pulse sequence.

14. A method according to claim 13, where the inversion-recovery or saturation-recovery imaging pulse sequence is a flow-independent dark-blood delayed enhancement sequence.

15. A method according to claim 11, where the scout pulse sequence is executed during free breathing of a patient being imaged.

16. A method according to claim 11, wherein determining one of the plurality of images comprises determining the one of the plurality of images which exhibits maximal separation of infarct myocardium and normal myocardium.

17. A method according to claim 16, wherein determining one of the plurality of images comprises determining the one of the plurality of images in which the normal myocardium is dark grey.

18. A non-transitory computer-readable medium storing program code, the program code executable by a computer system, configured to cause the computer system to:
determine an inversion-recovery or saturation-recovery imaging pulse sequence associated with first values of echo spacing and flip angle, each data acquisition of the inversion-recovery or saturation-recovery imaging pulse sequence to acquire a different set of a first number of image data lines of an image;
execute a scout pulse sequence comprising a plurality of single-shot image data acquisitions to acquire respective sets of image data lines, where each of the plurality of single-shot image data acquisitions is executed using a different respective inversion time and acquires a same set of the first number of image data lines, and where each of the plurality of single-shot image data acquisitions is associated with second values of echo spacing and flip angle which are substantially the same as corresponding ones of the first values;
generate a plurality of images, wherein each of the plurality of images is generated based on a respective one of the sets of image data lines and on no other sets of image data lines;
determine one of the plurality of images, the determined one of the plurality of images generated based on a first set of image data lines acquired using a first inversion time; and
execute the inversion-recovery or saturation-recovery imaging pulse sequence using the first inversion time.

19. A medium according to claim 18, wherein each of the plurality of single-shot image data acquisitions acquires a same set of the first number of k-space image data lines.

20. A medium according to claim 18, wherein determining one of the plurality of images comprises determining the one of the plurality of images which exhibits maximal separation of infarct myocardium and normal myocardium and in which the normal myocardium is dark grey.

* * * * *